US008629171B2

(12) United States Patent
Kim et al.

(10) Patent No.: US 8,629,171 B2
(45) Date of Patent: Jan. 14, 2014

(54) CRYSTALLINE FORM OF METHYL ((1S)-1-((2S)-2-(5-(4'-(2-((2S)-1((2S)-2-((METHOXYCARBONYL)AMINO)-3-METHYLBUTANOYL)-2-PYRROLIDINYL)-1H-IMIDAZOL-2-YL)-1-PYRROLIDINYL)CARBONYL)-2-METHYLPROPYL)CARBAMATE DIHYDROCHLORIDE SALT

(75) Inventors: Soojin Kim, Demarest, NJ (US); Qi Gao, Wallingford, CT (US); Fukang Yang, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 734 days.

(21) Appl. No.: 12/175,104

(22) Filed: Jul. 17, 2008

(65) Prior Publication Data

US 2009/0041716 A1 Feb. 12, 2009

Related U.S. Application Data

(60) Provisional application No. 60/954,592, filed on Aug. 8, 2007.

(51) Int. Cl.
*A61K 31/4178* (2006.01)
*C07D 233/54* (2006.01)

(52) U.S. Cl.
USPC ........................................ 514/397; 548/313.1

(58) Field of Classification Search
USPC ..................... 548/314.7, 313.1; 514/397, 400
See application file for complete search history.

(56) References Cited

U.S. PATENT DOCUMENTS 5,654,451 A    8/1997   Kari

FOREIGN PATENT DOCUMENTS

| WO | WO 94/15909 | 7/1994 |
|---|---|---|
| WO | WO2004/005264 A2 | 1/2004 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/077186 | 7/2007 |
| WO | WO 2007/138242 | 12/2007 |
| WO | WO 2008/021927 | 2/2008 |
| WO | WO 2008/021928 | 2/2008 |
| WO | WO 2008/021936 | 2/2008 |
| WO | WO 2008/133753 | 11/2008 |

OTHER PUBLICATIONS

Bastin, Richard J. Salt Selection and Optimization Procedures for Pharmaceutical New Chemical Entities. Organic Process Research and Development. 2000, 4, 427-435.*
U.S. Appl. No. 12/029,680, filed Feb. 12, 2008, Bachand et al.
U.S. Appl. No. 12/030,232, filed Feb. 13, 2008, Bachand et al.
U.S. Appl. No. 12/120,494, filed May 14, 2008, Bachand et al.
U.S. Appl. No. 12/174,860, filed Jul. 17, 2008, Pack et al.
U.S. Appl. No. 11/835,462 First Office Action, Aug. 15, 2008.
U.S. Appl. No. 11/835,462 Final Office Action, Jun. 2, 2009.
U.S. Appl. No. 11/835,462 Decision of Appeal, Feb. 2, 2011.
U.S. Appl. No. 12/644,852 First Office Action, Jan. 10, 2011.

* cited by examiner

*Primary Examiner* — Samantha Shterengarts
(74) *Attorney, Agent, or Firm* — Pamela A. Mingo

(57) ABSTRACT

The present disclosure generally relates to a crystalline form of methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate dihydrochloride salt. The present disclosure also generally relates to a pharmaceutical composition comprising a crystalline form, as well of methods of using a crystalline form in the treatment of Hepatitis C and methods for obtaining such crystalline form.

25 Claims, 3 Drawing Sheets

CRYSTALLINE FORM OF METHYL ((1S)-1-((2S)-2-(5-(4'-(2-((2S)-1-((2S)-2-((METHOXYCARBONYL)AMINO)-3-METHYLBUTANOYL)-2-PYRROLIDINYL)-1H-IMIDAZOL-2-YL)-1-PYRROLIDINYL)CARBONYL)-2-METHYLPROPYL) CARBAMATE DIHYDROCHLORIDE SALT

CROSS-REFERENCE TO RELATED APPLICATIONS

This application claims the benefit of U.S. Provisional Application Ser. No. 60/954,592 filed Aug. 8, 2007.

The present disclosure generally relates to a crystalline form of methyl ((1S)-1-(((2S)-2-(5-(4'-(2-((2S)-1-((2S)-2-((methoxycarbonyl)amino)-3-methylbutanoyl-2-pyrrolidinyl)-1H-imidazol-5-yl)-4-biphenylyl)-1H-imidazol-2-yl)-1-pyrrolidinyl)carbonyl)-2-methylpropyl)carbamate dihydrochloride salt. The present disclosure also generally relates to a pharmaceutical composition comprising a crystalline form, as well as methods of using a crystalline form in the treatment of Hepatitis C virus (HCV) and methods for obtaining such crystalline form.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40 percent of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

The compound methyl ((is)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl) carbamate is useful for the treatment of HCV infection. Due to the difficulty in crystallizing this compound, formation of pure product has not been reproducible. It has been found that the dihydrochloride salt, represented by formula (I) and herein referred to as Compound (I), can be repeatedly crystallized into one particular polymorph, herein referred to as Form N-2, that offers high aqueous solubility and excellent purification capacity.

Compound (I)

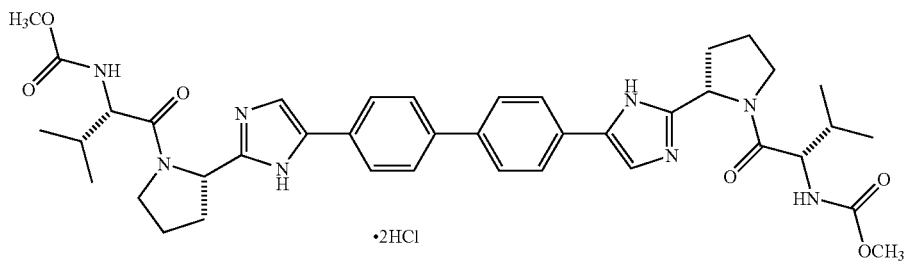 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

In its first aspect the present disclosure provides Form N-2 of

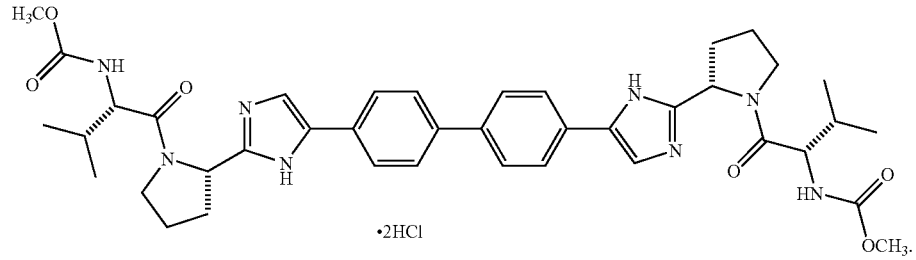 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

In a second aspect the present disclosure provides Form N-2 of

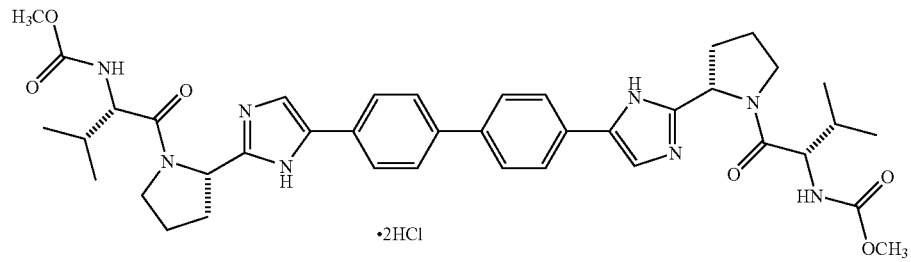 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

characterized by the following unit cell parameters:
Cell dimensions: a=7.5680 Å
b=9.5848 Å
c=16.2864 Å
α=74.132 degrees
β=84.132 degrees
γ=70.646 degrees Space group P1
Molecules/unit cell 1
wherein measurement of said crystalline form is at a temperature between about 20° C. to about 25° C.

In a third aspect the present disclosure provides Form N-2 of

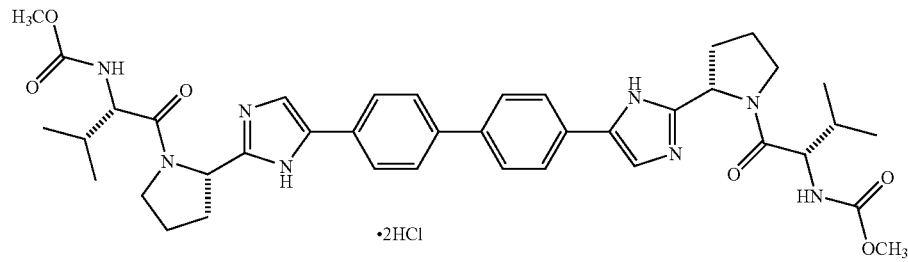

characterized by fractional atomic coordinates within the unit cell as listed in Table 3.

In a fourth aspect the present disclosure provides Form N-2 of

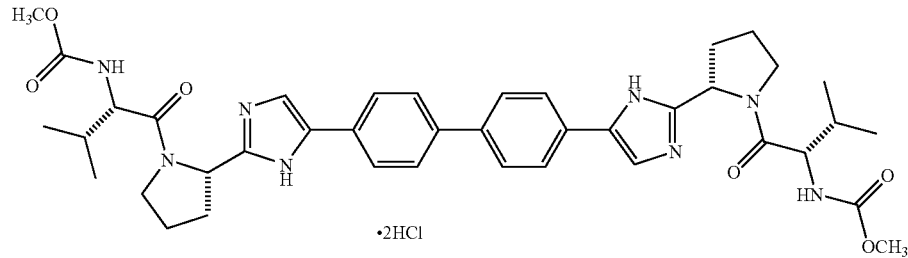 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

with characteristic peaks in the powder X-Ray diffraction pattern at values of two theta of 10.3±0.1, 12.4±0.1, 12.8±0.1, 13.3±0.1, 13.6±0.1, 15.5±0.1, 20.3±0.1, 21.2±0.1, 22.4±0.1, 22.7±0.1, and 23.7±0.1 at a temperature between about 20° C. and about 25° C., based on a high quality pattern collected with a diffractometer (CuKα) with a spinning capillary with 2θ calibrated with a NIST other suitable standard.

In a fifth aspect the present disclosure provides Form N-2 of

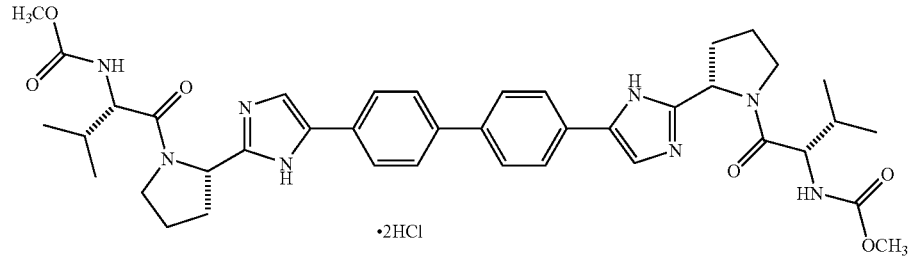 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

characterized by one or more of the following:
a) a unit cell with parameters substantially equal to the following:
Cell dimensions: a=7.5680 Å
b=9.5848 Å
c=16.2864 Å
α=74.132 degrees β=84.132 degrees
γ=70.646 degrees
Space group P1
Molecules/unit cell 1
wherein measurement of said crystalline form is at a temperature between about 20° C. to about 25° C.;
b) characteristic peaks in the powder X-Ray diffraction pattern at values of two theta of 10.3±0.1, 12.4±0.1, 12.8±0.1, 13.3±0.1, 13.6±0.1, 15.5±0.1, 20.3±0.1, 21.2±0.1, 22.4±0.1, 22.7±0.1, and 23.7±0.1 at a temperature between about 20° C. and about 25° C., based on a high quality pattern collected with a diffractometer (CuKα) with a spinning capillary with 2θ calibrated with a NIST other suitable standard; and/or
c) a melt with decomposition endotherm with onset typically in the range of 225-245° C.

In a sixth aspect the present disclosure provides substantially pure Form N-2 of

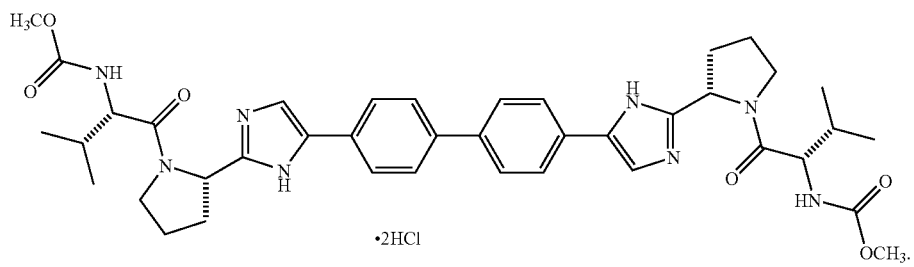 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

In a first embodiment of the sixth aspect said Form N-2 has a purity of at least 95 weight percent. In a second embodiment of the sixth aspect said Form N-2 has a purity of at least 99 weight percent.

In a seventh aspect the present disclosure provides substantially pure Form N-2 of

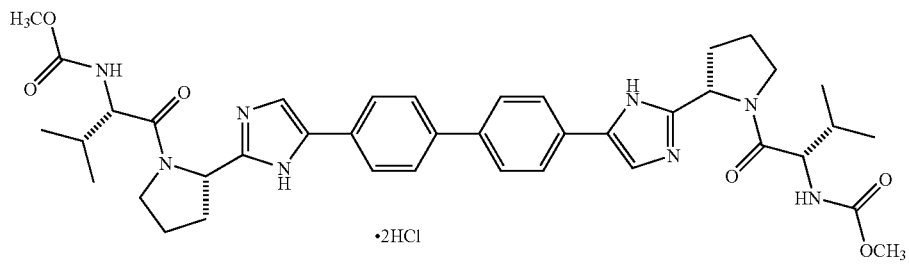

with characteristic peaks in the powder X-Ray diffraction pattern at values of two theta of 10.3±0.1, 12.4±0.1, 12.8±0.1, 13.3±0.1, 13.6±0.1, 15.5±0.1, 20.3±0.1, 21.2±0.1, 22.4±0.1, 22.7±0.1, and 23.7±0.1 at a temperature between about 20° C. and about 25° C., based on a high quality pattern collected with a diffractometer (CuKα) with a spinning capillary with 2θ calibrated with a NIST other suitable standard.

In an eighth aspect the present disclosure provides a pharmaceutical composition comprising Form N-2 of

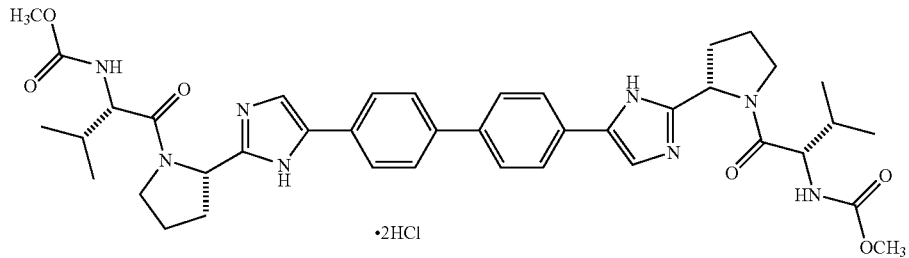 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

and a pharmaceutically acceptable carrier or diluent.

In a ninth aspect the present disclosure provides a pharmaceutical composition comprising substantially pure Form N-2 of

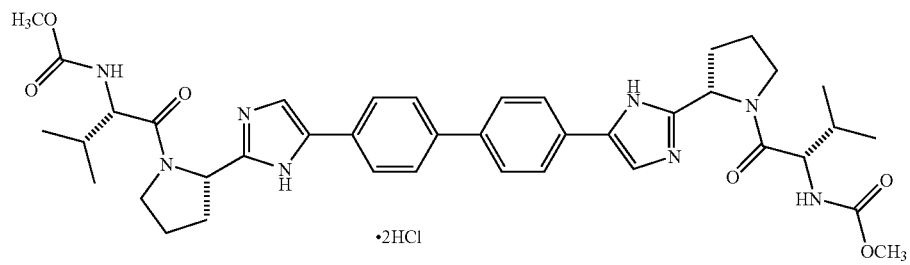

and a pharmaceutically acceptable carrier or diluent. In a first embodiment of the ninth aspect said Form N-2 has a purity of at least 95 weight percent. In a second embodiment of the ninth aspect said Form N-2 has a purity of at least 99 weight percent.

In a tenth aspect the present disclosure provides a pharmaceutical composition comprising Form N-2 of

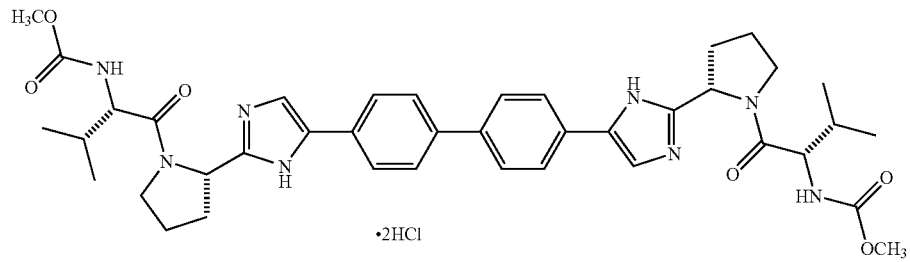

in combination with one or two additional compounds having anti-HCV activity. In a first embodiment of the tenth aspect said Form N-2 has a purity of at least 90 weight percent. In a second embodiment of the tenth aspect said Form N-2 has a purity of at least 95 weight percent. In a third embodiment of the tenth aspect said Form N-2 has a purity of at least 99 weight percent.

In a fourth embodiment of the tenth aspect at least one of the additional compounds having anti-HCV activity is an interferon or ribavirin. In a fifth embodiment of the tenth aspect the interferon is selected from interferon alpha 2B, pegylated interferon alpha, consensus interferon, interferon alpha 2A, and lymphoblastiod interferon tau.

In a sixth embodiment of the tenth aspect the present disclosure provides a pharmaceutical composition comprising Form N-2 of

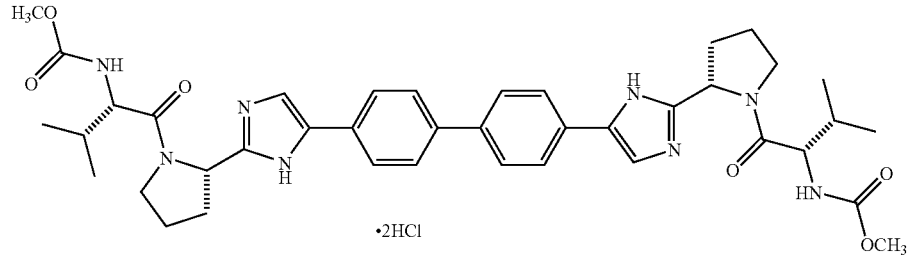 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

in combination with one or two additional compounds having anti-HCV activity wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In an eleventh aspect the present disclosure provides a method of treating HCV infection in a mammal comprising administering to the mammal a therapeutically-effective amount of Form N-2 of

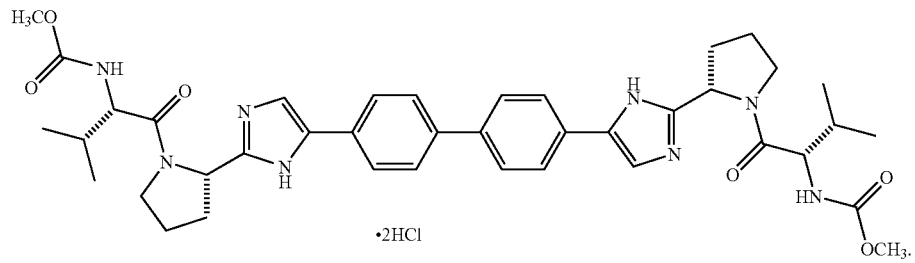 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

In a first embodiment of the eleventh aspect said Form N-2 has a purity of at least 90 weight percent. In a second embodiment of the eleventh aspect said Form N-2 has a purity of at least 95 weight percent. In a third embodiment of the eleventh aspect said Form N-2 has a purity of at least 99 weight percent. In a fourth embodiment of the eleventh aspect the mammal is a human.

Other embodiments of the present disclosure may comprise suitable combinations of two or more of embodiments and/or aspects disclosed herein.

Yet other embodiments and aspects of the disclosure will be apparent according to the description provided below.

The compounds of the present disclosure also exist as tautomers; therefore the present disclosure also encompasses all tautomeric forms.

Figure 1:
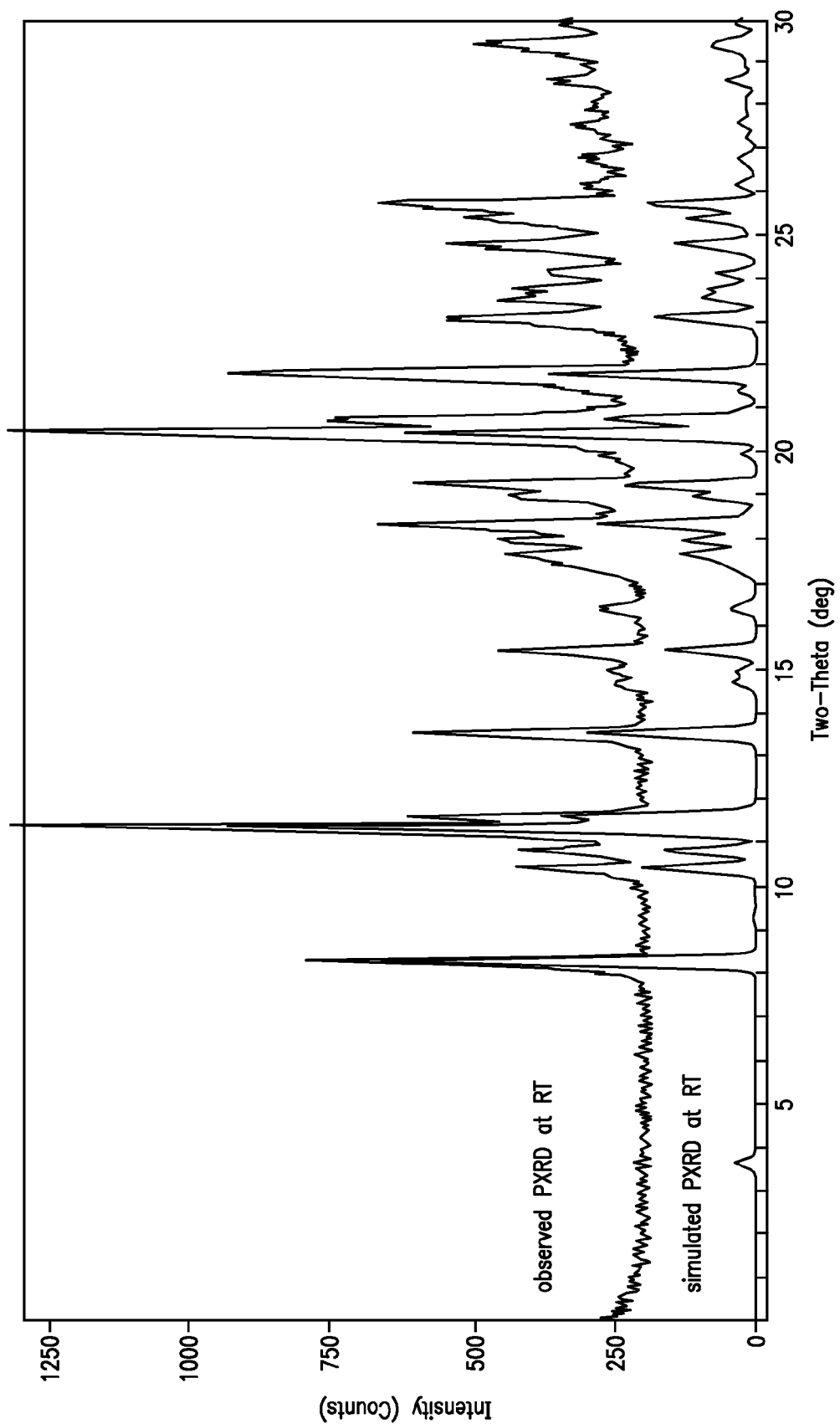
FIG. 1 illustrates experimental and simulated powdered X-Ray diffraction patterns (CuKα λ=1.54178 Å at T=room temperature) of the N-2 crystalline form of Compound (I).

The disclosure relates to a crystalline form of Compound (I).

The term "pharmaceutically acceptable," as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The term "substantially pure," as used herein refers to Form N-2 of Compound (I) which is great than about 90% pure. This means that the polymorph of Compound (I) does not contain more than about 10% of any other compound, and, in particular, does not contain more than about 10% of any other form of Compound (I).

The term "therapeutically effective amount," as used herein, is intended to include an amount of the crystalline forms of Compound (I) that is effective when administered alone or in combination to treat Hepatitis C. The crystalline forms of Compound (I) and pharmaceutical compositions thereof may be useful in treating Hepatitis C. If Compound (I) is used in combination with another medication, the combination of compounds described herein may result in a synergistic combination. Synergy, as described for example by Chou and Talalay, *Adv. Enzyme Regul.* 1984, 22, 27-55, occurs when the effect of the compounds when administered in combination is greater than the effect of the compounds when administered alone as single agents.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

In one embodiment the disclosure provides a crystalline form of Compound (I). This crystalline form of Compound (I)

(I)

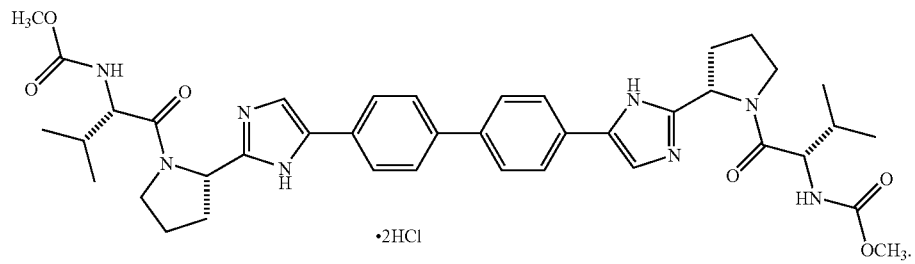 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

DEFINITIONS

As used herein "polymorph" refers to crystalline forms having the same chemical composition but different spatial arrangements of the molecules, atoms, and/or ions forming the crystal.

may be employed in pharmaceutical compositions which may optionally include one or more other components selected, for example, from the group consisting of excipients, carriers, and one of other active pharmaceutical ingredients active chemical entities of different molecular structure.

In one embodiment the crystalline form has phase homogeneity indicated by less than 10 percent, in another embodiment the crystalline form has phase homogeneity indicated by less than 5 percent, and in another embodiment the crystalline form has phase homogeneity indicated by less than 2 percent of the total peak area in the experimentally measured PXRD pattern arising from the extra peaks that are absent from the simulated PXRD pattern. In another embodiment the crystalline form has phase homogeneity with less than 1 percent of the total peak area in the experimentally measured PXRD pattern arising from the extra peaks that are absent from the simulated PXRD pattern.

In one embodiment, a composition is provided consisting essentially of the crystalline form N-2 of Compound (I). The composition of this embodiment may comprise at least 90 weight percent of the crystalline form N-2 of Compound (I), based on the weight of Compound (I) in the composition. The remaining material comprises other form(s) of the compound and/or reaction impuritis and/or processing impurities arising from its preparation.

The presence of reaction impurities and/or processing impurities may be determined by analytical techniques known in the art, such as, for example, chromatography, nuclear magnetic resonance spectroscopy, mass spectrometry, or infrared spectroscopy.

General Preparation of Crystalline Materials:

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs. Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to control effectively the growth of crystals in the batch. Seed of small size may be generated by sieving, milling, or micronizing of large crystals, or by microcrystallization of solutions. Care should be taken that milling or micronizing of crystals does not result in any change in crystallinity of the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, X-Ray powder diffraction, or the like, to assure formation of the preferred crystalline form of the product. The resulting crystalline form is typically produced in an amount of greater than about 70 weight percent isolated yield, preferably greater than 90 weight percent isolated yield, based on the weight of the compound originally employed in the crystallization procedure. The product may be co-milled or passed through a mesh screen to delump the product, if necessary.

Crystalline forms may be prepared directly from the reaction medium of the final process for preparing Compound (I). This may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned non-polar solvents and polar solvents, including protic polar solvents such as alcohols, and aprotic polar solvents such as ketones.

The presence of more than one polymorph in a sample may be determined by techniques such as powder X-Ray diffraction (PXRD) or solid state nuclear magnetic resonance spectroscopy (SSNMR). For example, the presence of extra peaks in an experimentally measured PXRD pattern when compared with a simulated PXRD pattern may indicate more than one polymorph in the sample. The simulated PXRD may be calculated from single crystal X-Ray data. see Smith, D. K., "*A FORTRAN Program for Calculating X-Ray Powder Diffraction Patterns*," Lawrence Radiation Laboratory, Livermore, Calif., UCRL-7196 (April 1963).

Characterization:

Form N-2 of Compound (I) can be characterized using various techniques, the operation of which are well known to those of ordinary skill in the art. Examples of characterization methods include, but are not limited to, single crystal X-Ray diffraction, powder X-Ray diffraction (PXRD), simulated powder X-Ray patterns (Yin, S.; Scaringe, R. P.; DiMarco, J.; Galella, M. and Gougoutas, J. Z., *American Pharmaceutical Review*, 2003, 6, 2, 80), differential scanning calorimetry (DSC), solid-state $^{13}$C NMR (Earl, W. L. and Van der Hart, D. L., *J. Magn. Reson.*, 1982, 48, 35-54), Raman spectroscopy, infrared spectroscopy, moisture sorption isotherms, thermal gravimetric analysis (TGA), and hot stage techniques.

The forms may be characterized and distinguished using single crystal X-Ray diffraction, which is based on unit cell measurements of a single crystal of form N-2. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder X-Ray diffraction analysis in which the diffraction profile is compared to a simulated profile representing pure powder material, both run at the same analytical temperature, and measurements for the subject form characterized as a series of 2θ values.

One of ordinary skill in the art will appreciate that an X-Ray diffraction pattern may be obtained with a measurement of error that is dependent upon the measurement conditions employed. In particular, it is generally known that intensities in an X-Ray diffraction pattern may fluctuate depending upon measurement conditions employed. It should be further understood that relative intensities may also vary depending upon experimental conditions, and, accordingly, the exact order of intensity should not be taken into account. Additionally, a measurement error of diffraction angle for a conventional X-Ray diffraction pattern is typically about 5 percent or less, and such degree of measurement error should be taken into account as pertaining to the aforementioned diffraction angles. Consequently, it is to be understood that the crystal forms of the present disclosure are not limited to the crystal forms that provide X-Ray diffraction patterns completely identical to the X-Ray diffraction patterns depicted in the accompanying Figures disclosed herein. Any crystal form that provides and X-Ray diffraction pattern, DSC thermogram, or SSNMR spectrum substantially identical to those disclosed in the accompanying Figures fall within the scope of the present disclosure. The ability to ascertain substantial identities of X-Ray diffraction patters is within the purview of one of ordinary skill in the art.

Utility:

The N-2 form of Compound (I), alone or in combination with other compounds, can be used to treat HCV infection.

The present disclosure also provides compositions comprising a therapeutically effective amount of the N-2 form of Compound (I) and at least one pharmaceutically acceptable carrier.

The active ingredient, i.e., form N-2 of Compound (I), in such compositions typically comprises from 0.1 weight percent to 99.9 percent by weight of the composition, and often comprises from about 5 to 95 weight percent. In some cases, the pH of the formulation may be adjusted with pharmaceutically acceptable modifiers (such as calcium carbonate and magnesium oxide) to enhance the stability of the formulated compound or its delivery form. Formulations of the polymorph of the present disclosure may also contain additives for enhancement of absorption and bioavailability.

The pharmaceutical compositions of this disclosure may be administered orally, parenterally or via an implanted reservoir. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents and suspending agents. The details concerning the preparation of such compounds are known to those skilled in the art.

When orally administered, the pharmaceutical compositions of this disclosure may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, can also be added. For oral administration in a capsule form, useful carriers/diluents include lactose, high and low molecular weight polyethylene glycol, and dried corn starch. When aqueous suspensions are administered orally, the active ingredient is combined with emulsifying and suspending agents. If desired, certain sweetening and/or flavoring and/or coloring agents may be added.

Other suitable carriers for the above noted compositions can be found in standard pharmaceutical texts, e.g. in "Remington's Pharmaceutical Sciences", 19th ed., Mack Publishing Company, Easton, Pa., 1995. Further details concerning the design and preparation of suitable delivery forms of the pharmaceutical compositions of the disclosure are known to those skilled in the art.

Dosage levels of between about 0.05 and about 100 milligram per kilogram ("mg/kg") body weight per day, more specifically between about 0.1 and about 50 mg/kg body weight per day of the compounds of the disclosure are typical in a monotherapy for the prevention and/or treatment of HCV mediated disease. Typically, the pharmaceutical compositions of this disclosure will be administered from about 1 to about 3 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, gender, diet, time of administration, the duration of treatment, rate of excretion, drug combination, the severity and course of the infection, the patient's disposition to the infection and the judgment of the treating physician. In one embodiment, unit dosage formulations are those containing a daily dose or sub-dose, as herein above recited, or an appropriate fraction thereof, of an active ingredient. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of the polymorph of the disclosure and one or more additional therapeutic or prophylactic agents, both the compound and the additional agent are usually present at dosage levels of between about 10 and 100 percent, and more preferably between about 10 and 80 percent of the dosage normally administered in a monotherapy regimen. Administration of the one or more additional agents may occur prior to, after, or simultaneously with the polymorph of the present disclosure.

When the polymorph is formulated together with a pharmaceutically acceptable carrier, the resulting composition may be administered in vivo to mammals, such as man, to inhibit NS5A or to treat or prevent HCV virus infection. Such treatment may also be achieved using the polymorph of this disclosure in combination with agents which include, but are not limited to: Immunomodulatory agents, such as interferons; other antiviral agents such as ribavirin, amantadine; other inhibitors of NS5A; inhibitors of other targets in the- HCV life cycle such as helicase, protease, polymerase, metalloprotease, or internal ribosome entry site; or combinations thereof. The additional agents may be combined with the polymorph of this disclosure to create a single dosage form. Alternatively these additional agents may be separately administered to a mammal as part of a multiple dosage form.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |

TABLE 1-continued

| Brand Name | Physiological Class | Type of Inhibitor or Target | Source Company |
|---|---|---|---|
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |

TABLE 1-continued

| Brand Name | Physiological Class | Type of Inhibitor or Target | Source Company |
|---|---|---|---|
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |

Another aspect of this disclosure provides methods of inhibiting HCV NS5A activity in patients by administering the polymorph of the present disclosure.

In one embodiment, these methods are useful in decreasing HCV NS5A activity in the patient. If the pharmaceutical composition comprises only the polymorph of this disclosure as the active component, such methods may additionally comprise the step of administering to said patient an agent selected from an immunomodulatory agent, an antiviral agent, an HCV NS5A inhibitor, or an inhibitor of other targets in the HCV life cycle such as, for example, helicase, polymerase, protease, or metalloprotease. Such additional agent may be administered to the patient prior to, concurrently with, or following the administration of the compounds of this disclosure.

In another embodiment, these methods are useful for inhibiting viral replication in a patient. Such methods can be useful in treating or preventing HCV disease.

The polymorph of the disclosure may also be used as a laboratory reagent. The polymorph may be instrumental in providing research tools for designing of viral replication assays, validation of animal assay systems and structural biology studies to further enhance knowledge of the HCV disease mechanisms.

The polymorph of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

The following non-limiting examples are illustrative of the disclosure.

EXAMPLES

Preparation of Compound 2

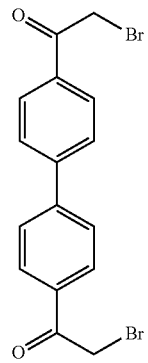

A 1 L, 3-neck round bottom flask, fitted with a nitrogen line, overhead stirrer and thermocouple, was charged with 20 g (83.9 mmol, 1 equiv) 1,1'-(biphenyl-4,4'-diyl)diethanone, 200 mL CH$_2$Cl$_2$ and 8.7 mL (27.1 g, 169.3 mmol, 2.02 quiv) bromine. The mixture was allowed to stir under nitrogen for about 20 hours under ambient conditions. The resulting slurry was charged with 200 mL CH$_2$Cl$_2$ and concentrated down to about 150 mL via vacuum distillation. The slurry was then solvent exchanged into THF to a target volume of 200 mL via vacuum distillation. The slurry was cooled to 20-25° C. over 1 hour and allowed to stir at 20-25° C. for an additional hour. The off-white crystalline solids were filtered and washed with 150 mL CH$_2$Cl$_2$. The product was dried under vacuum at 60° C. to yield 27.4 g (69.2 mmol, 82%) of the desired product: $^1$H NMR (400 MHz, CDCl$_3$) δ 7.95-7.85 (m, 4H), 7.60-7.50 (m, 4H), 4.26 (s, 4H); $^{13}$C NMR (100 MHz, CDCl$_3$) δ 191.0, 145.1, 133.8, 129.9, 127.9, 30.8; IR (KBr, cm−1) 3007, 2950, 1691, 1599, 1199; Anal calcd for C$_{16}$H$_{12}$Br$_2$O$_2$: C, 48.52; H, 3.05; Br, 40.34. Found: C, 48.53; H, 3.03; Br, 40.53 HRMS calcd for C$_{16}$H$_{13}$Br$_2$O$_2$ (M+H; DCI$^+$): 394.9282. Found: 394.9292. mp 224-226° C.

Preparation of Compound 3

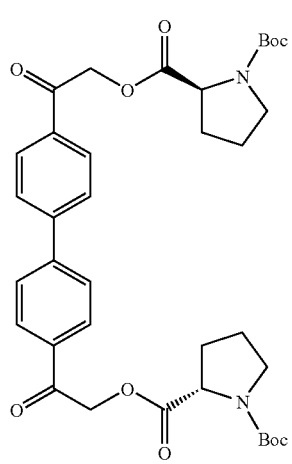

A 500 mL jacketed flask, fitted with a nitrogen line, thermocouple and overhead stirrer, was charged with 20 g (50.5 mmol, 1 equiv) of Compound 2, 22.8 g (105.9 moles, 2.10 equiv) 1-(tert-butoxycarbonyl)-L-proline and 200 mL acetonitrile. The slurry was cooled to 20° C. followed by the addition of 18.2 mL (13.5 g, 104.4 mmol, 2.07 equiv) DIPEA. The slurry was warmed to 25° C. and allowed to stir for 3 hours. The resulting clear, organic solution was washed with 3×100 mL 13 wt % aqueous NaCl. The rich acetonitrile solution was solvent exchanged into toluene (target volume=215 mL) by vacuum distillation until there was less than 0.5 vol % acetonitrile.

Preparation of Compound 4

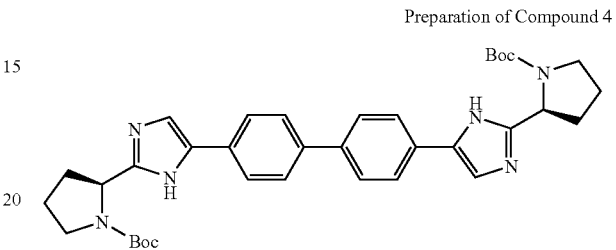

The toluene solution of Compound 3 was charged with 78 g (1.011 moles, 20 equiv) ammonium acetate and heated to 95-100° C. The mixture was allowed to stir at 95-100° C. for 15 hours. After reaction completion, the mixture was cooled to 70-80° C. and charged with 7 mL acetic acid, 40 mL n-butanol, and 80 mL of 5 vol % aqueous acetic acid. The resulting biphasic solution was split while maintaining a temperature >50° C. The rich organic phase was charged with 80 mL of 5 vol % aqueous acetic acid, 30 mL acetic acid and 20 mL n-butanol while maintaining a temperature >50° C. The resulting biphasic solution was split while maintaining a temperature >50° C. and the rich organic phase was washed with an additional 80 mL of 5 vol % aqueous acetic acid. The rich organic phase was then solvent exchanged into toluene to a target volume of 215 mL by vacuum distillation. While maintaining a temperature >60° C., 64 mL methanol was charged. The resulting slurry was heated to 70-75° C. and aged for 1 hour. The slurry was cooled to 20-25° C. over 1 hour and aged at that temperature for an additional hour. The slurry was filtered and the cake was washed with 200 mL 10:3 toluene: methanol. The product was dried under vacuum at 70° C., resulting in 19.8 g (31.7 mmol, 63%) of the desired product: $^1$H NMR (400 MHz, DMSO-d$_6$) δ 13.00-11.00 (s, 2H), 7.90-7.75 (m, 4H), 7.75-7.60 (m, 4H), 7.60-7.30 (s, 2H), 4.92-4.72 (m, 2H), 3.65-3.49 (m, 2H), 3.49-3.28 (m, 2H), 2.39-2.1 (m, 2H), 2.10-1.87 (m, 6H), 1.60-1.33 (s, 8H), 1.33-1.07 (s, 10H); $^{13}$C NMR (100 MHz, DMSO-d$_6$) δ 154.1, 153.8, 137.5, 126.6, 125.0, 78.9, 78.5, 55.6, 55.0, 47.0, 46.7, 33.7, 32.2, 28.5, 28.2, 24.2, 23.5; IR (KBr, cm−1) 2975, 2876, 1663, 1407, 1156, 1125; HRMS calcd for C$_{36}$H$_{45}$N$_6$O$_4$ (M+H; ESI$^+$): 625.3502. Found: 625.3502. mp 190-195° C. (decomposed).

Preparation of Compound 5

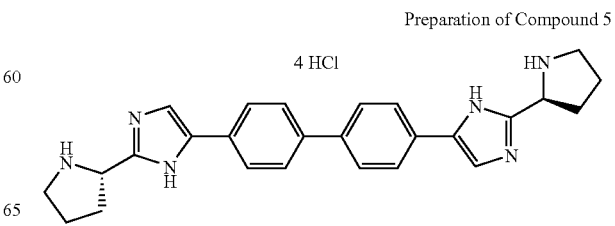

To a 250 mL reactor equipped with a nitrogen line and overhead stirrer, 25.0 g of Compound 4 (40.01 mmol, 1 equiv) was charged followed by 250 mL methanol and 32.85 mL (400.1 mmol, 10 equiv) 6M aqueous HCl. The temperature was increased to 50° C. and agitated at 50° C. for 5 hours. The resulting slurry was cooled to 20-25° C. and held with agitation for about 18 hours. Filtration of the slurry afforded a solid which was washed successively with 100 mL 90% methanol/water (V/V) and 2×100 mL of methanol. The wet cake was dried in a vacuum oven at 50° C. overnight to give 18.12 g (31.8 mmol, 79.4%) of the desired product.

Recrystallization of Compound 5

To a 250 mL reactor equipped with a nitrogen line and an overhead stirrer, 17.8 g of Compound 5 from above was charged followed by 72 mL methanol. The resulting slurry was agitated at 50° C. for 4 hours, cooled to 20-25° C. and held with agitation at 20-25° C. for 1 hour. Filtration of the slurry afforded a crystalline solid which was washed with 60 mL methanol. The resulting wet cake was dried in a vacuum oven at 50° C. for 4 days to yield 14.7 g (25.7 mmol, 82.6%) of the purified product: $^1$H NMR (400 MHz, DMSO-$d_6$) δ 10.5-10.25 (br, 2H), 10.1-9.75 (br, 2H), 8.19 (s, 2H), 7.05 (d, J=8.4, 4H), 7.92 (d, J=8.5, 4H), 5.06 (m, 2H), 3.5-3.35 (m, 4H), 2.6-2.3 (m, 4H), 2.25-2.15 (m, 2H), 2.18-1.96 (m, 2H); $^{13}$C NMR (100 MHz, DMSO-$d_6$) δ 156.6, 142.5, 139.3, 128.1, 127.5, 126.1, 116.9, 53.2, 45.8, 29.8, 24.3; IR (KBr, cm$^{-1}$) 3429, 2627, 1636, 1567, 1493, 1428, 1028. Anal calcd for $C_{26}H_{32}N_6Cl_4$: C, 54.75; H, 5.65; Cl, 24.86; Adjusted for 1.9% water: C, 53.71; H, 5.76; N, 14.46; Cl, 24.39. Found: C, 53.74; H, 5.72; N, 14.50; Cl, 24.49; KF=1.9. mp 240° C. (decomposed).

nopropyl)-3-ethylcarbodiimide hydrochloride and an additional 100 mL acetonitrile. The resulting solution was agitated at 20° C. for 1 hour and charged with 20.4 g (35.8 mmol, 1 equiv) of purified Compound 5. The slurry was cooled to about 0° C. and 18.47 g (142.9 mmol, 4 equiv) diisopropylethylamine was added over 30 minutes while maintaining a temperature below 10° C. The solution was slowly heated to 15° C. over 3 hours and held at 15° C. for 12 hours. The resulting solution was charged with 120 mL 13 wt % aqueous NaCl and heated to 50° C. for 1 hour. After cooling to 20° C., 100 mL of isopropyl acetate was added. The biphasic solution was filtered through a 0.45 μm filter and the mixture split. The rich organic phase was washed with 2×240 mL of a 0.5 N NaOH solution containing 13 wt % NaCl followed by 120 mL 13 wt % aqueous NaCl. The mixture was then solvent exchanged into isopropyl acetate by vacuum distillation with a target volume of 400 mL. The resulting hazy solution was cooled to 20° C. and filtered through a 0.45 μm filter. The clear solution was then solvent exchanged into ethanol by vacuum distillation with a target volume of 140 mL. While maintaining a temperature of 50° C., 66.4 mL (82.3 mmol, 2.3 equiv) of 1.24M HCl in ethanol was added. The mixture was then charged with 33 mg (0.04 mmol, 0.001 equiv) of seed crystals of Compound (I) (see preparation below) and the resulting slurry was stirred at 50° C. for 3 hours. The mixture was cooled to 20° C. over 1 hour and aged at that temperature for an additional 22 hours. The slurry was filtered and the wet cake was washed with 100 mL of 2:1 acetone:ethanol. The solids were dried in a vacuum oven at 70° C. to give 22.15 g (27.3 mmol, 76.3%) of the desired product.

Preparation of Compound (I)

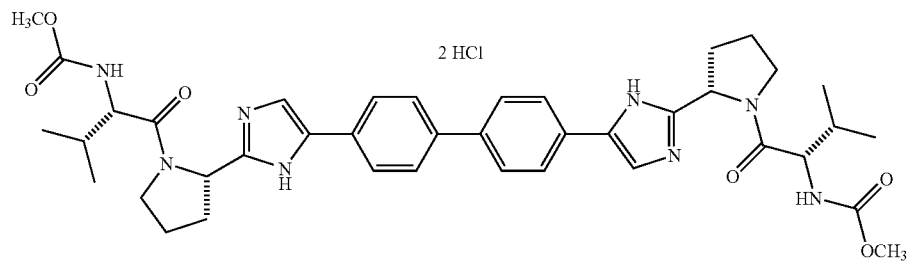

A 1 L jacketed flask equipped with a nitrogen line and an overhead stirrer was sequentially charged with 100 mL acetonitrile, 13.69 g (89.4 mmol, 2.5 equiv) hydroxybenzotriazole hydrate, 15.07 g (86 mmol, 2.4 equiv) N-(methoxycarbonyl)-L-valine, 16.46 g (85.9 mmol, 2.4 equiv) 1-(3-dimethyami- Carbon Treatment and Recrystallization of Compound (I)

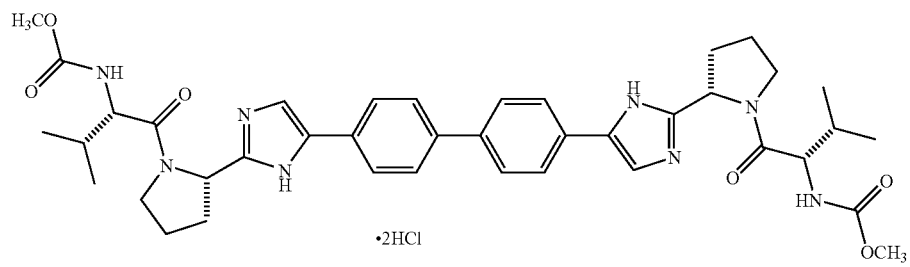 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

A solution of Compound (I) was prepared by dissolving 3.17 g of Compound (I) from above in 22 mL methanol. The solution was passed through a 47 mm Cuno Zeta Carbon® 53SP filter at ~5 psig at a flow rate of ~58 mL/min. The carbon filter was rinsed with 32 mL of methanol. The solution was concentrated down to 16 mL by vacuum distillation. While maintaining a temperature of 40-50° C., 15.9 mL acetone and 5 mg of seed crystals of Compound (I) (see procedure below) were added. The resulting slurry was then charged with 32 mL acetone over 30 minutes. The slurry was held at 50° C. for 2 hours, cooled to 20° C. over about 1 hour and held at 20° C. for about 20 hours. The solids were filtered, washed with 16 mL 2:1 acetone:methanol and dried in a vacuum oven at 60° C. to give 2.14 g (67.5%) of purified Compound (I): $^1$H NMR (400 MHz, DMSO-$d_6$, 80° C.): 8.02 (d, J=8.34 Hz, 4H), 7.97 (s, 2H), 7.86 (d, J=8.34 Hz, 4H), 6.75 (s, 2H), 5.27 (t, J=6.44 Hz, 2H), 4.17 (t, J=6.95 Hz, 2H), 3.97-4.11 (m, 2H), 3.74-3.90 (m, 2H), 3.57 (s, 6H), 2.32-2.46 (m, 2H), 2.09-2.31 (m, 6H), 1.91-2.07 (m, 2H), 0.88 (d, J=6.57 Hz, 6H), 0.79 (d, J=6.32 Hz, 6H); $^{13}$C NMR (75 MHz, DMSO-$d_6$): δ 170.9, 156.9, 149.3, 139.1, 131.7, 127.1, 126.5, 125.9, 115.0, 57.9, 52.8, 51.5, 47.2, 31.1, 28.9, 24.9, 19.6, 17.7; IR (neat, cm$^{-1}$): 3385, 2971, 2873, 2669, 1731, 1650. Anal. Calcd for $C_{40}H_{52}N_8O_6Cl_2$: C, 59.18; H, 6.45; N, 13.80; Cl, 8.73. Found C, 59.98; H, 6.80; N, 13.68; Cl, 8.77. mp 267° C. (decomposed).

Preparation of Seed Crystals of Compound (I)

A 250 mL round-bottom flask was charged with 6.0 g (10.5 mmol, 1 equiv) Compound 5, 3.87 g (22.1 mmol, 2.1 equiv) N-(methoxycarbonyl)-L-valine, 4.45 g (23.2 mmol, 2.2 equiv) 1-(3-dimethyaminopropyl)-3-ethylcarbodiimide hydrochloride, 0.289 g (2.14 mmol, 0.2 equiv) 1-hydroxybenzotriazole, and 30 mL acetonitrile. The resulting slurry was then charged with 7.33 mL (42.03 mmol, 4 equiv) diisopropylethylamine and allowed to stir at 24-30° C. for about 18 hours. The mixture was charged with 6 mL of water and heated to 50° C. for about 5 hours. The mixture was cooled and charged with 32 mL ethyl acetate and 30 mL water. The layers were separated and the rich organic layer was washed with 30 mL of 10 wt % aqueous $NaHCO_3$, 30 mL water, and 20 mL of 10 wt % aqueous NaCl. The rich organic layer was then dried over $MgSO_4$, filtered, and concentrated down to a residue. The crude material was then purified via flash chromatography (silica gel, 0-10% methanol in dichloromethane) to provide the free base of Compound (I).

The free-base of Compound (I) (0.03 g) was dissolved in 1 mL isopropanol at 20° C. Anhydrous HCl (70 μL, dissolved in ethanol, approximately 1.25M concentration) was added and the reaction mixture was stirred. To the solution was added methyl tert-butyl ether (1 mL) and the resulting slurry was stirred vigorously at 40° C. to 50° C. for 12 hours. The crystal slurry was cooled to 20° C. and filtered. The wet cake was air-dried at 20° C. A white crystalline solid (Form N-2 of Compound (I)) was obtained.

Form N-2 was analyzed using one or more of the testing methods described below.

1 Single Crystal X-Ray Measurements

A Bruker APEX2 Kappa CCD diffractometer equipped with a rotating anode generator of Cu Kα radiation, (λ=1.54178 Å) was used to collect diffraction data at the room temperature. Indexing and processing of the measured intensity data were carried out with the APEX2 software package/program suite (APEX2 Data collection and processing user interface: APEX2 User Manual, v1.27; BRUKER AXS, INc., 5465 East Cheryl Parkway, Madison, Wis. 53711 USA). The final unit cell parameters were determined using the entire data set.

The structure was solved by direct methods and refined by the full-matrix least-squares techniques, using the SHELXTL software package (Sheldrick, G M. 1997, SHELXTL. Structure Determination Programs. Version 5.10, Bruker AXS, Madison, Wis., USA.). The function minimized in the refinements was $\Sigma w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|Fo|^2]^{1/2}$, where w is an appropriate weighting function based on errors in the observed intensities. Difference Fourier maps were examined at all stages of refinement. All non-hydrogen atoms were refined with anisotropic thermal displacement parameters. The hydrogen atoms associated with hydrogen bonding were located in the final difference Fourier maps while the positions of the other hydrogen atoms were calculated from an idealized geometry with standard bond lengths and angles. They were assigned isotropic temperature factors and included in structure factor calculations with fixed parameters.

The crystal data of the N-2 form is shown in Table 2. The fractional atomic coordinates are listed in Table 3. It should be understood by one of ordinary skill in the art that slight variations in the coordinates are possible and are considered to be within the scope the present disclosure.

TABLE 2

| Crystal Data of Form N-2 | |
|---|---|
| Temperature | room temperature |
| Wavelength | 1.54178 Å |
| Crystal system, space group | Triclinic, P1 |
| Unit cell dimensions | a = 7.5680(2) Å alpha = 74.132(2)° |
| | b = 9.5848(3) Å beta = 84.132(2)° |
| | c = 16.2864(5) Å gamma = 70.646(2)° |
| Volume | 1072.06(5) Å$^3$ |
| Z, Calculated density | 1, 1.257 Mg/m$^3$ |

TABLE 3

| Atomic coordinates | | | | | | | |
|---|---|---|---|---|---|---|---|
| Atom | X | Y | Z | Atom | X | Y | Z |
| C7 | 0.0807 | −0.0688 | 0.0165 | H3 | 0.0264 | 0.2281 | −0.0035 |
| C16 | −0.5489 | 0.4635 | −0.1121 | H17 | −0.7884 | 0.4046 | −0.0848 |
| C4 | −0.0807 | 0.0688 | −0.0165 | H2 | −0.2192 | 0.4393 | −0.0575 |
| C18 | −0.7034 | 0.6975 | −0.1863 | H5 | −0.2549 | −0.0380 | −0.0365 |
| C13 | 0.5516 | −0.4628 | 0.1105 | H6 | −0.5015 | 0.1728 | −0.0892 |
| C15 | 0.7037 | −0.6988 | 0.1841 | H9 | 0.5090 | −0.1737 | 0.0755 |
| C3 | −0.0789 | 0.2157 | −0.0218 | H14 | 0.7875 | −0.4013 | 0.0906 |
| C10 | 0.3885 | −0.3317 | 0.0771 | H12 | −0.0376 | −0.2264 | 0.0165 |
| C1 | −0.3895 | 0.3303 | −0.0781 | H11 | 0.2109 | −0.4403 | 0.0683 |
| C17 | −0.7335 | 0.4794 | −0.1115 | H8 | 0.2590 | 0.0389 | 0.0270 |
| C2 | −0.2275 | 0.3428 | −0.0531 | H19 | 0.8664 | −0.8827 | 0.2693 |
| C5 | −0.2458 | 0.0584 | −0.0412 | H20A | 0.6721 | −0.9411 | 0.1489 |
| C6 | −0.3950 | 0.1847 | −0.0720 | H20B | 0.8848 | −1.0218 | 0.1745 |
| C9 | 0.3978 | −0.1858 | 0.0641 | H22A | 0.4299 | −0.9831 | 0.2863 |
| C14 | 0.7330 | −0.4774 | 0.1143 | H22B | 0.5433 | −1.0623 | 0.3720 |
| C12 | 0.0728 | −0.2143 | 0.0290 | H24 | 0.4288 | −0.8972 | 0.4553 |
| C11 | 0.2233 | −0.3439 | 0.0597 | H29A | 0.3610 | −0.6896 | 0.7199 |
| C8 | 0.2471 | −0.0573 | 0.0347 | H29B | 0.5410 | −0.6388 | 0.7042 |
| C19 | 0.7480 | −0.8565 | 0.2404 | H29C | 0.5552 | −0.8060 | 0.7046 |
| C20 | 0.7591 | −0.9804 | 0.1959 | H26A | 0.0099 | −0.5669 | 0.3086 |
| C22 | 0.5494 | −1.0075 | 0.3126 | H26B | 0.2158 | −0.5619 | 0.2923 |
| C24 | 0.3932 | −0.7895 | 0.4232 | H26C | 0.1027 | −0.5160 | 0.3723 |
| C28 | 0.4299 | −0.7573 | 0.5628 | H25 | 0.2074 | −0.8105 | 0.3478 |
| C29 | 0.4783 | −0.7007 | 0.6895 | H21A | 0.6629 | −1.1660 | 0.2427 |
| C26 | 0.1249 | −0.5830 | 0.3353 | H21B | 0.8099 | −1.1619 | 0.3036 |
| C25 | 0.1972 | −0.7461 | 0.3866 | H27A | 0.0368 | −0.7163 | 0.4938 |

TABLE 3-continued

Atomic coordinates

| Atom | X | Y | Z | Atom | X | Y | Z |
|------|---|---|---|------|---|---|---|
| C21 | 0.7052 | −1.0999 | 0.2661 | H27B | 0.1093 | −0.8874 | 0.4894 |
| C27 | 0.0588 | −0.7834 | 0.4569 | H27C | −0.0572 | −0.7699 | 0.4319 |
| C23 | 0.5435 | −0.7711 | 0.3553 | H30 | −0.6271 | 0.8706 | −0.2714 |
| C30 | −0.7440 | 0.8547 | −0.2454 | H31A | −0.9249 | 0.9498 | −0.1547 |
| C34 | −0.8171 | 0.7743 | −0.3628 | H31B | −0.7674 | 1.0278 | −0.1856 |
| C31 | −0.8522 | 0.9853 | −0.2037 | H33A | −1.1460 | 0.9828 | −0.2916 |
| C33 | −1.0373 | 1.0092 | −0.3191 | H33B | −1.0659 | 1.0635 | −0.3783 |
| C32 | −0.9782 | 1.1019 | −0.2736 | H32A | −1.0859 | 1.1679 | −0.2499 |
| C38 | −0.8340 | 0.7734 | −0.5748 | H32B | −0.9111 | 1.1645 | −0.3120 |
| C36 | −1.1117 | 0.7288 | −0.3922 | H36 | −1.1758 | 0.7856 | −0.3502 |
| C39 | −0.6953 | 0.7302 | −0.7067 | H39A | −0.7874 | 0.7037 | −0.7301 |
| C37 | −1.0485 | 0.5605 | −0.3464 | H39B | −0.5733 | 0.6820 | −0.7276 |
| C35 | −0.9477 | 0.7893 | −0.4312 | H39C | −0.7221 | 0.8392 | −0.7235 |
| N1 | 0.5385 | −0.6067 | 0.1537 | H37A | −1.1562 | 0.5276 | −0.3279 |
| N4 | −0.5358 | 0.6044 | −0.1590 | H37B | −0.9757 | 0.5444 | −0.2977 |
| N2 | 0.8232 | −0.6215 | 0.1585 | H37C | −0.9736 | 0.5027 | −0.3846 |
| N3 | −0.8254 | 0.6252 | −0.1572 | H35 | −0.9995 | 0.8976 | −0.4608 |
| N6 | −0.8719 | 0.8722 | −0.3123 | H1 | 0.4378 | −0.6316 | 0.1597 |
| N5 | 0.5974 | −0.8687 | 0.3055 | H4 | −0.4338 | 0.6276 | −0.1688 |
| N8 | −0.8375 | 0.7087 | −0.4913 | H2A | 0.9413 | −0.6576 | 0.1685 |
| N7 | 0.3941 | −0.6991 | 0.4812 | H3A | −0.9442 | 0.6631 | −0.1654 |
| O4 | −0.6651 | 0.6742 | −0.3518 | H8A | −0.7710 | 0.6146 | −0.4726 |
| O1 | 0.6094 | −0.6663 | 0.3446 | H7 | 0.3699 | −0.6020 | 0.4611 |
| O2 | 0.4413 | −0.8890 | 0.6028 | H40A | −1.1909 | 0.7164 | −0.5066 |
| O3 | 0.4448 | −0.6524 | 0.5991 | H40B | −1.3113 | 0.8675 | −0.4819 |
| O5 | −0.9383 | 0.8955 | −0.6125 | H40C | −1.3481 | 0.7128 | −0.4362 |
| O6 | −0.7001 | 0.6782 | −0.6138 | | | | |
| C40 | −1.2538 | 0.7592 | −0.4606 | | | | |
| C11 | −0.2486 | 0.7587 | −0.1475 | | | | |
| C12 | 0.2421 | −0.7524 | 0.1377 | | | | |

2. Powder X-Ray Diffraction

About 200 mg were packed into a Philips powder X-ray diffraction (PXRD) sample holder. The sample was transferred to a Philips MPD unit (45 KV, 40 mA, Cu Kα). Data were collected at room temperature in the 2 to 32 2θ range (continuous scanning mode, scanning rate 0.03 degrees/sec., auto divergence and anti scatter slits, receiving slit: 0.2 mm, sample spinner: ON).

The results of the PXRD pattern and a simulated pattern calculated from the single crystal data are shown in FIG. 1.

Table 4 lists the characteristic PXRD peaks that describe Form N-2 of Compound (I).

TABLE 4

Characteristic diffraction peak positions (degrees 2θ ± 0.1) at room temperature, based on a high quality pattern collected with a diffractometer (cuKα) with a spinning capillary with 2θ calibrated with a NIST other suitable standard.
Form N-2

| |
|---|
| 10.3 |
| 12.4 |
| 12.8 |
| 13.3 |
| 13.6 |
| 15.5 |
| 20.3 |
| 21.2 |
| 22.4 |
| 22.7 |
| 23.7 |

3. Differential Scanning Calorimetry

Differential scanning calorimetry (DSC) experiments were performed in a TA Instruments™ model Q2000, Q1000 or 2920. The sample (about 2-6 mg) was weighed in an aluminum pan and recorded accurately to a hundredth of a milligram, and transferred to the DSC. The instrument was purged with nitrogen gas adt 50 mL/min. Data were collected between room temperature and 300° C. at 10° C./min heating rate. The plot was made with the endothermic peaks pointing down.

Figure 2:
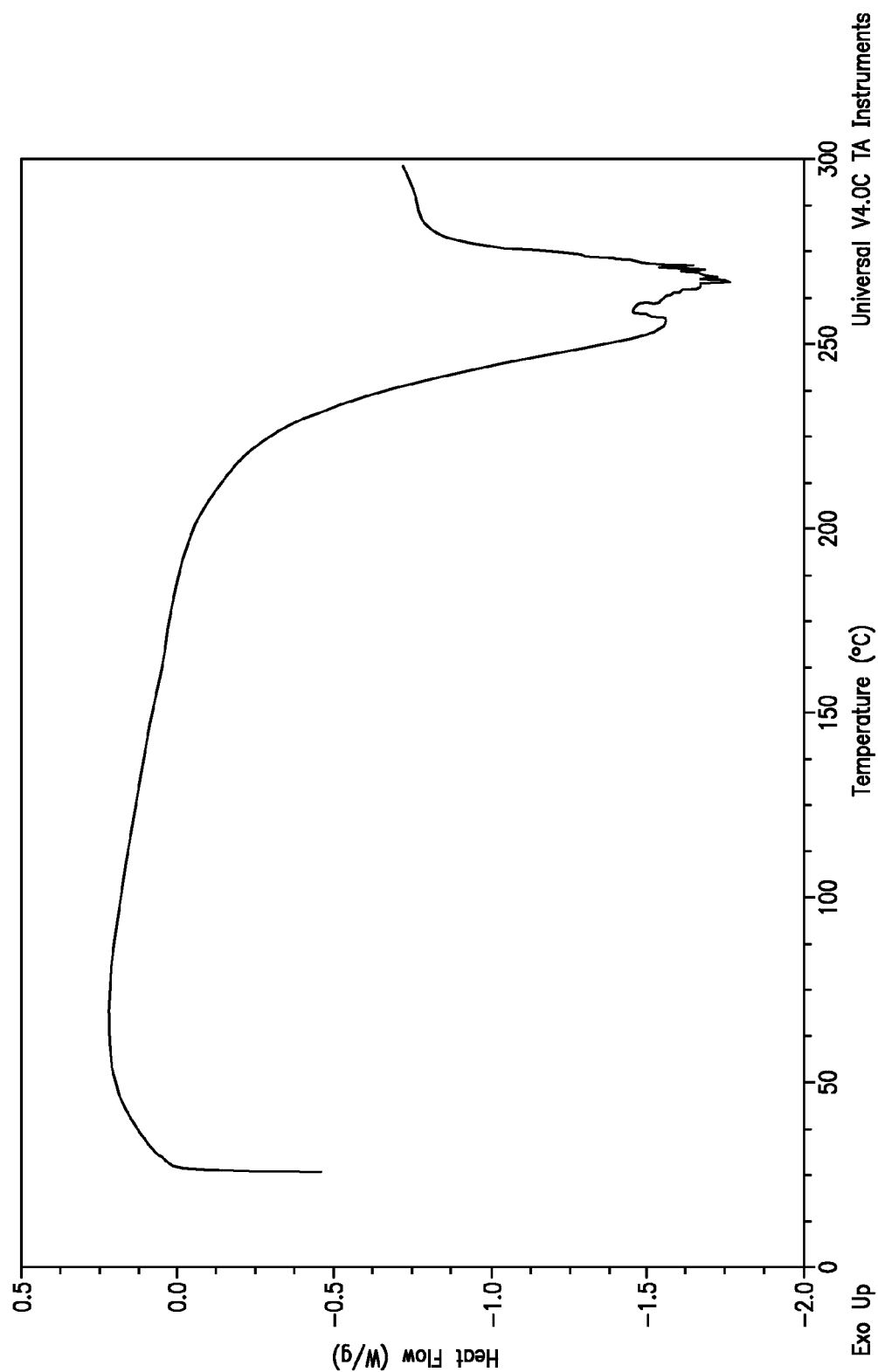
FIG. 2 illustrates the differential scanning calorimetry pattern of the N-2 crystalline form of Compound (I).

The results are shown in FIG. 2.

4. Solid-State NMR (SSNMR)

All solid-state C-13 NMR measurements were made with a Bruker DSX-400, 400 MHz NMR spectromter. High resolution spectra were obtained using high-power proton decoupling and the TPPM pulse sequence and ramp amplitude cross-polarization (RAMP-CP) with magic-angle spinning (MAS) at approximately 12 kHz (A. E. Bennett et al. *J. Chem. Phys.* 1995, 103, 6951). (G. Metz, X. Wu, and S. O. Smith, *J. Magn. Reson. A.*, 1994, 110, 219-227). Approximately 70 mg of sample, packed into a canister-design zirconia rotor was used for each experiment. Chemical shifts (δ) were referenced to external adamantane with the high frequency resonance being set to 38.56 ppm (W. L. Earl and D. L. VanderHart, *J. Magn. Reson.*, 1982, 48, 35-54).

Figure 3:
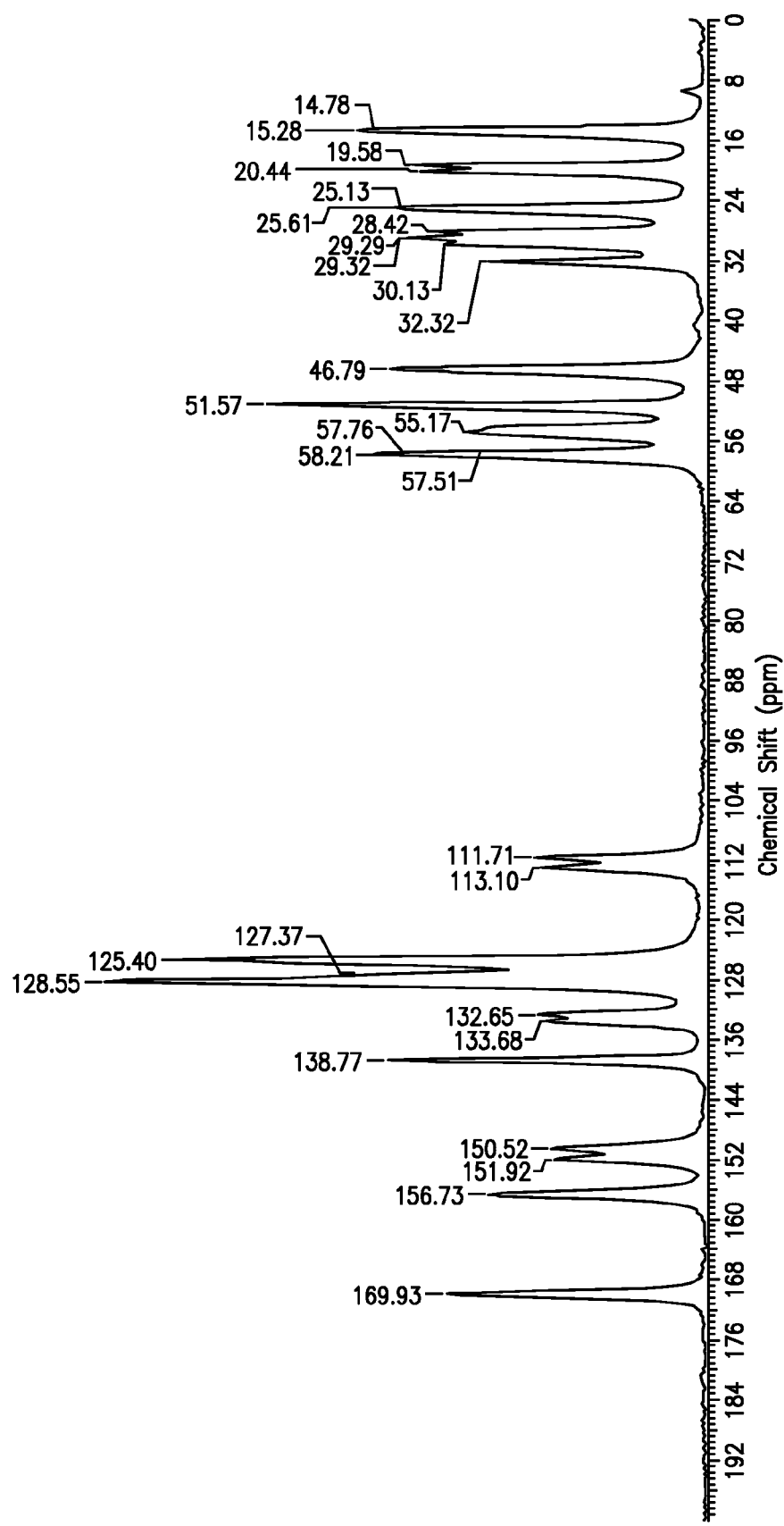
FIG. 3 illustrates the solid state NMR spectrum of the N-2 crystalline form of Compound (I).

The SSNMR spectrum is shown in FIG. 3.

Table 5 lists the characteristic SSNMR peaks that describe Form N-2 of Compound (I).

TABLE 5

SSNMR peak positions of Form N-2 of Compound (I). Peak positions δ (in ppm) relative to TMS scale.
Form N-2

| |
|---|
| 14.8 |
| 15.3 |
| 19.6 |
| 20.4 |
| 25.1 |
| 25.6 |
| 28.4 |
| 29.3 |
| 29.3 |
| 30.1 |
| 32.3 |
| 46.8 |
| 51.6 |
| 54.3 |
| 55.2 |
| 57.5 |
| 57.8 |
| 58.2 |
| 111.7 |
| 113.1 |
| 125.4 |
| 127.4 |
| 128.5 |
| 132.6 |
| 133.7 |
| 138.8 |
| 150.5 |
| 151.9 |
| 156.7 |
| 169.9 |

What is claimed is:
1. Form N-2 of

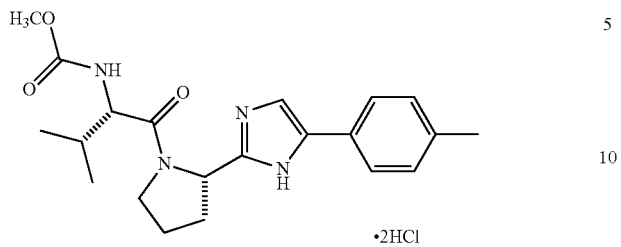

2. Form N-2 of

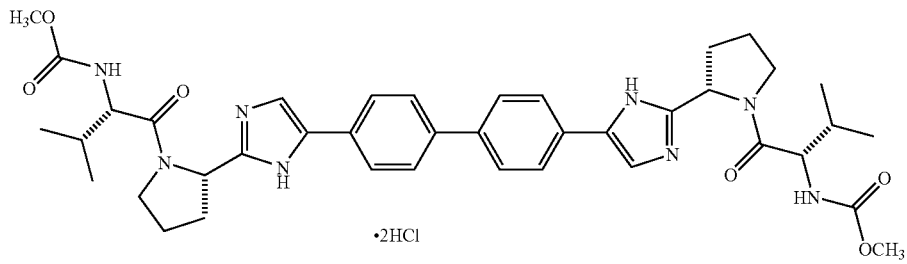 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

characterized by the following unit cell parameters:
   Cell dimensions: a=7.5680 Å
   b=9.5848 Å
   c=16.2864 Å
   α=74.132 degrees
   β=84.132 degrees
   γ=70.646 degrees
   Space group P1
   Molecules/unit cell 1
wherein measurement of said crystalline form is at a temperature between about 20° C. to about 25° C.

3. Form N-2 of

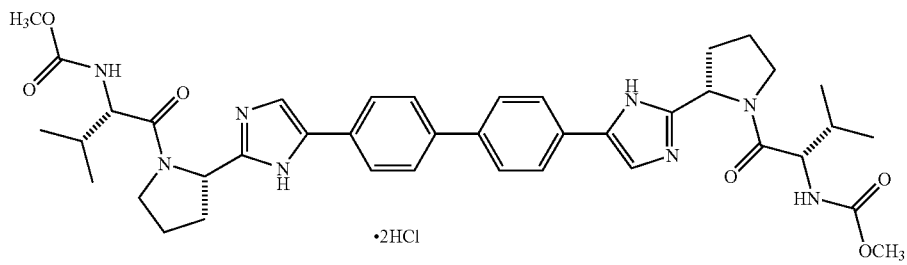 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

characterized by fractional atomic coordinates within the unit cell as listed in Table 3.

4. Form N-2 of

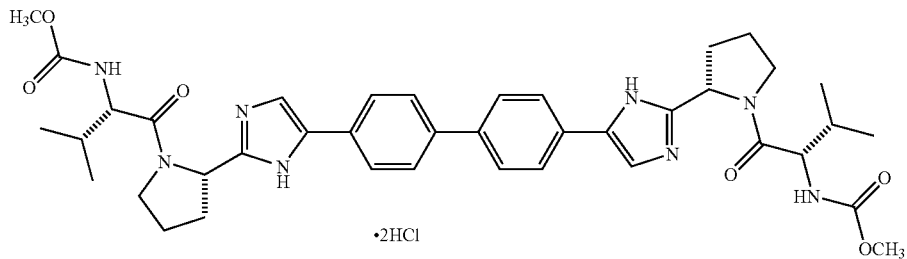 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

•2HCl with characteristic peaks in the powder X-Ray diffraction pattern at values of two theta of 10.3±0.1, 12.4±0.1, 12.8±0.1, 13.3±0.1, 13.6±0.1, 15.5±0.1, 20.3±0.1, 21.2±0.1, 22.4±0.1, 22.7±0.1, and 23.7±0.1 at a temperature between about 20° C. and about 25° C.

5. Form N-2 of

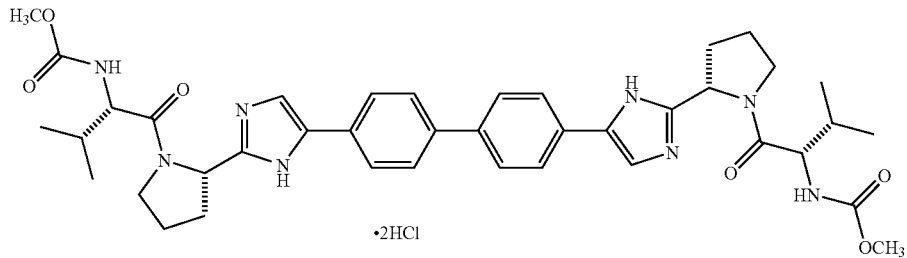

•2HCl characterized by one or more of the following:
a) a unit cell with parameters substantially equal to the following:
Cell dimensions: a=7.5680 Å
b=9.5848 Å
c=16.2864 Å
α=74.132 degrees
β=84.132 degrees
γ=70.646 degrees
Space group P1
Molecules/unit cell 1
wherein measurement of said crystalline form is at a temperature between about 20° C. to about 25° C.;
b) characteristic peaks in the powder X-Ray diffraction pattern at values of two theta of 10.3±0.1, 12.4±0.1, 12.8±0.1, 13.3±0.1, 13.6±0.1, 15.5±0.1, 20.3±0.1, 21.2±0.1, 22.4±0.1, 22.7±0.1, and 23.7±0.1 at a temperature between about 20° C. and about 25° C.; and/or
c) a melt with decomposition endotherm with onset typically in the range of 225-245° C.

6. Substantially pure Form N-2 of

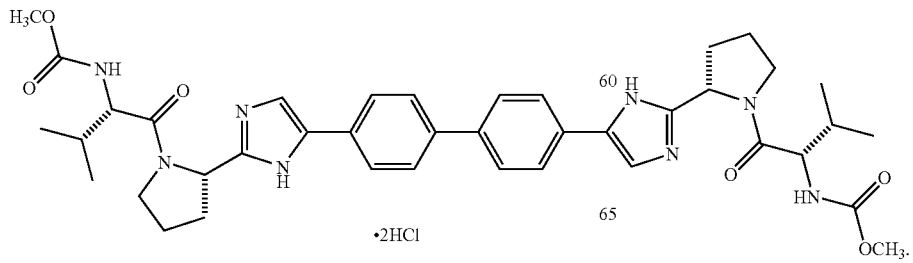

•2HCl

7. The form of claim 6 wherein said Form N-2 has a purity of at least 95 weight percent.

8. The form of claim 6 wherein said Form N-2 has a purity of at least 99 weight percent.

9. Substantially pure Form N-2 of

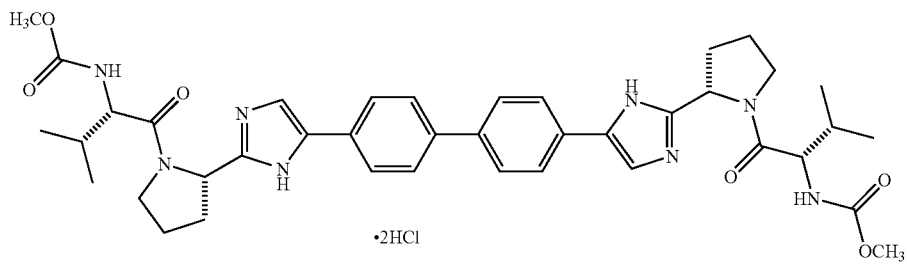 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

with characteristic peaks in the powder X-Ray diffraction pattern at values of two theta of 10.3±0.1, 12.4±0.1, 12.8±0.1, 13.3±0.1, 13.6±0.1, 15.5±0.1, 20.3±0.1, 21.2±0.1, 22.4±0.1, 22.7±0.1, and 23.7±0.1 at a temperature between about 20° C. and about 25° C.

10. A pharmaceutical composition comprising Form N-2 of

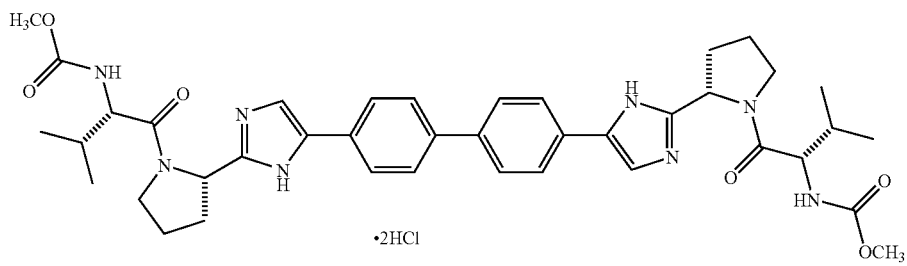 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

and a pharmaceutically acceptable carrier or diluent.

11. A pharmaceutical composition comprising substantially pure Form N-2 of

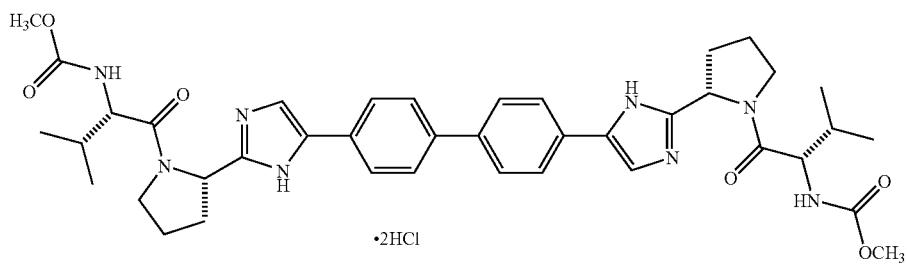 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

and a pharmaceutically acceptable carrier or diluent.

12. The pharmaceutical composition of claim 11 wherein said Form N-2 has a purity of at least 95 weight percent.

13. The pharmaceutical composition of claim 11 wherein said Form N-2 has a purity of at least 99 weight percent.

14. A pharmaceutical composition comprising Form N-2 of

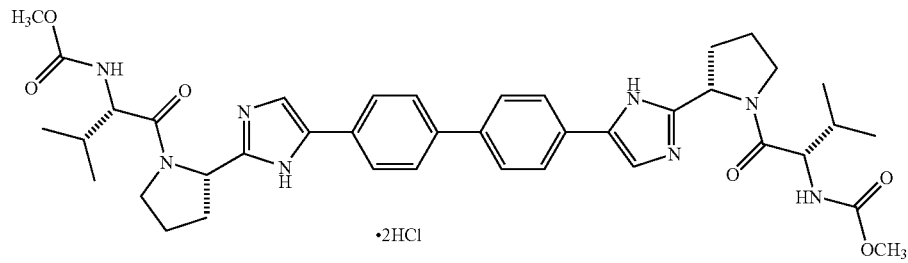 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

in combination with one or two additional compounds, wherein the one or two additional compounds have anti-HCV activity.

15. The pharmaceutical composition of claim 14 wherein said Form N-2 has a purity of at least 90 weight percent.

16. The pharmaceutical composition of claim 14 wherein said Form N-2 has a purity of at least 95 weight percent.

17. The pharmaceutical composition of claim 14 wherein said Form N-2 has a purity of at least 99 weight percent.

18. The composition of claim 14 wherein at least one of the additional compounds having anti-HCV activity is an interferon or ribavirin.

19. The composition of claim 18 wherein the interferon is selected from interferon alpha 2B, pegylated interferon alpha, consensus interferon, interferon alpha 2A, and lymphoblastiod interferon tau.

20. The composition of claim 14 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

21. A method of inhibiting HCV infection in a mammal comprising administering to the mammal a therapeutically-effective amount of Form N-2 of

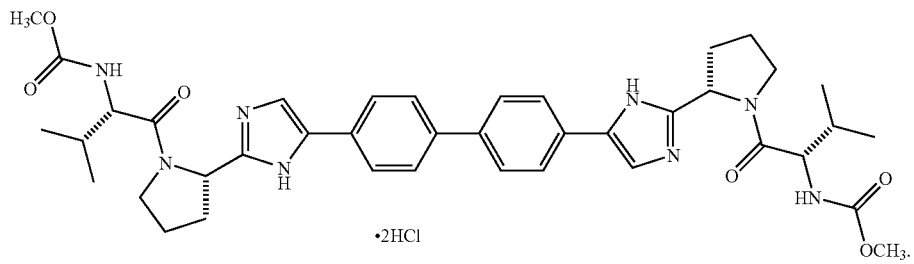 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C ; "·2HCl"]

22. The method of claim 21 wherein said Form N-2 has a purity of at least 90 weight percent.

23. The method of claim 21 wherein said Form N-2 has a purity of at least 95 weight percent.

24. The method of claim 21 wherein said Form N-2 has a purity of at least 99 weight percent.

25. The method of claim 21 wherein the mammal is a human.

* * * * *

UNITED STATES PATENT AND TRADEMARK OFFICE
CERTIFICATE OF CORRECTION

PATENT NO. : 8,629,171 B2  
APPLICATION NO. : 12/175104  
DATED : January 14, 2014  
INVENTOR(S) : Soojin Kim et al.

It is certified that error appears in the above-identified patent and that said Letters Patent is hereby corrected as shown below:

On the Title Page:

Item (54), and in the Specification, column 1, lines 1 to 7, change Title

"CRYSTALLINE FORM OF METHYL ((1S)-1-((2S)-2-(5-(4'-(2-((2S)-1((2S)-2-((METHOXYCARBONYL)AMINO)-3-METHYLBUTANOYL)-2-PYRROLIDINYL)-1H-IMIDAZOL-2-YL)-1-PYRROLIDINYL)CARBONYL)-2-METHYLPROPYL)CARBAMATE DIHYDROCHLORIDE SALT"

to

-- CRYSTALLINE FORM OF METHYL ((1S)-1-(((2S)-2-(5-(4'-(2-((2S)-1-((2S)-2-((METHOXYCARBONYL)AMINO)-3-METHYLBUTANOYL)-2-PYRROLIDINYL)-1H-IMIDAZOL-5-YL)-4-BIPHENYLYL)-1H-IMIDAZOL-2-YL)-1-PYRROLIDINYL)CARBONYL)-2-METHYLPROPYL)CARBAMATE DIHYDROCHLORIDE SALT --.

Item (57), ABSTRACT:

Column 2, line 8 (Abstract), change "as well" to -- as well as --.

In the Specification:

Column 7, line 50, change "lymphoblastiod" to -- lymphoblastoid --.

Column 9, line 6, change "Imiqimod," to -- Imiquimod, --.

Column 9, line 6, change "5'-monophospate" to -- 5'-monophosphate --.

Signed and Sealed this  
Thirty-first Day of March, 2015

Michelle K. Lee  
*Director of the United States Patent and Trademark Office*

CERTIFICATE OF CORRECTION (continued)
U.S. Pat. No. 8,629,171 B2

In the Claims:

Claim 19:

Column 36, lines 18 and 19, change "lymphoblastiod" to -- lymphoblastoid --.

Claim 20:

Column 36, line 24, change "Imiqimod," to -- Imiquimod, --.

UNITED STATES PATENT AND TRADEMARK OFFICE
CERTIFICATE OF CORRECTION

PATENT NO. : 8,629,171 B2
APPLICATION NO. : 12/175104
DATED : January 14, 2014
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1061 days.

Signed and Sealed this
Twelfth Day of May, 2015

Michelle K. Lee
*Director of the United States Patent and Trademark Office*